United States Patent [19]
Ward

[11] 3,973,025
[45] Aug. 3, 1976

[54] 1,4-DIHYDRO-3,5-PYRIDINE DICARBONITRILE DERIVATIVES

[75] Inventor: Terence James Ward, Slough, England

[73] Assignee: John Wyeth and Brother Limited, Maidenhead, England

[22] Filed: Apr. 29, 1975

[21] Appl. No.: 572,672

[30] Foreign Application Priority Data
May 17, 1974 United Kingdom............... 22451/74

[52] U.S. Cl............................... 424/263; 260/294.9
[51] Int. Cl.².......................................... A01N 9/22
[58] Field of Search.................. 260/294.9; 424/263

[56] References Cited
UNITED STATES PATENTS
3,511,847   5/1970   Loev et al..................... 260/295.5 R OTHER PUBLICATIONS
Palecek et al., Chem. Abstracts, vol. 71 (23), 112, 758a, Dec. 8, 1969.

*Primary Examiner*—Alan L. Rotman

[57] ABSTRACT

The invention relates to 3,5-dicyano-1,4-dihydro-2,6-di(lower)alkyl-4-methyl-4-phenylpyridines which have hypotensive activity.

4 Claims, No Drawings

1,4-DIHYDRO-3,5-PYRIDINE DICARBONITRILE DERIVATIVES

The invention relates to dihydropyridines, to processes for preparing the dihydropyridines and to pharmaceutical compositions containing them.

The novel dihydropyridines of the present invention are those of the general formula (I)

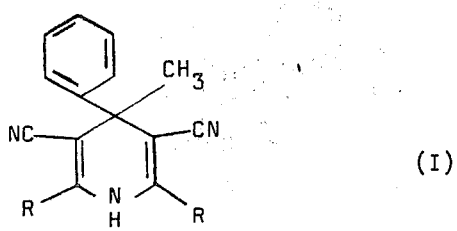

(I)

In general formula (I) each R is lower alkyl.

The term "lower" as used herein means that the radical contains from 1 to 4 carbon atoms. Thus each R group may be methyl, ethyl, propyl or butyl. Preferably both R groups are methyl. Thus a preferred compound of general formula (I) is 3,5-dicyano-1,4-dihydro-2,4,6-trimethyl-4-phenylpyridine. This compound can be in a substantially pure form. For example, it can be a form suitable for incorporation into pharmaceutical compositions. Substantially pure 3,5-dicyano-1,4-dihydro-2,4,6-trimethyl-4-phenylpyridine melts at about 195° to 196°C.

E. von Meyer in J. Prakt. Chem., 1915, 92, 174 describes the reaction of various ketones with nitrile compounds but he mentions that acetophenone only gave a dihydropyridine derivative when reacted with benzoacetodinitrile. Surprisingly it has now been found that the compounds of general formula (I) may be prepared by a process which comprises condensing acetophenone with an amino nitrile of general formula (II)

(II)

and isolating the product. Although preferable it is not essential to isolate the product in a substantially pure form.

In the reaction two molar equivalents of the amino nitrile react with one molar equivalent of acetophenone. It is preferable to use slightly more than the stoichiometric amount of the acetophenone. For example about 0.65 Mole of acetophenone may be reacted with about 1 Mole of the nitrile. The reaction may be carried out in an organic solvent in presence of an acid, e.g., hydrochloric acid. In the isolation of the product it is preferable to remove excess acetophenone by steam distillation. The product can then be extracted from the residue by known procedures.

The aminonitriles of general formula (II) are either known compounds or they can be prepared by standard procedures. For example they may be prepared by base catalysed condensation of acetonitrile with a nitrile of general formula (III)

RCN (III)

where R has the meaning given above, and isolation of the desired compound of formula (II) from the reaction medium by known procedures.

The compounds of the present invention exhibit hypotensive activity upon administration to warm-blooded animals according to standard test procedures. In one such test procedure 3,5-dicyano-1,4-dihydro-2,4,6,-trimethyl-4-phenylpyridine, a representative compound of the present invention, was found to produce a fall of at least 30 mm. mercury in the diastostolic blood pressure of anaesthetised normotensive rats when administered at 3.2 and 6.4 mg/kg. in duplicate experiments.

The invention further provides pharmaceutical compositions comprising a compound of general formula (I) in association with a pharmaceutically acceptable carrier.

Any suitable carrier known in the art can be used to prepare the pharmaceutical compositions. In such a composition, the carrier may be solid, liquid or mixture of a solid and a liquid. Solid form compositions include powders, tablets and capsules. A solid carrier can be one or more substances which may also act as flavoring agents, lubricants, solubilizers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired.

The powders and tablets preferably contain from 5 to 99, preferably 10–80% of the active ingredient. Suitable solid carriers are magnesium carbonate, magnesium stearate, talc, sugar, lactose, pectin, dextrin, starch gelatin, tragacanth, methyl cellulose, sodium carboxymethyl cellulose, a low melting wax, and cocoa butter. The term "composition" is intended to include the formulation of a active ingredient with encapsulating material as carrier to give a capsule in which the active ingredient (with or without other carriers) is surrounded by carrier, which is thus in association with it. Similarly cachets are included.

Sterile liquid from compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent,, for instance aqueous propylene glycol or polyethylene glycol solutions. Aqueous propylene glycol containing from 10 to 75% of the glycol by weight is generally suitable. In other instances compositions can be made by dispersing the finely divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form.

The quantity of active ingredient in a unit dose of composition may be carried or adjusted from about 5 mg. to 500 mg., according to the particular need and the activity of the active ingredient. The invention also includes the compounds in the absence of carrier where the compounds are in unit dosage form.

The following Example illustrates the invention:

EXAMPLE 3,5-Dicyano-1,4-dihydro-2,4,6,-trimethyl-4-phenylpyridine

A solution of ethanolic hydrogen chloride (10 ml., 5.25 molar) was added to a stirred solution of acetophenone (7.8 g, 0.065 mol.) and 3-aminocrotonitrile (8.2 g., 0.1 mol.; prepared according to Atkins et al., J. Amer. Chem. Soc.,) in ethanol (10 ml.), maintained below 20°C. The solution was then stoppered and stirred at room temperature for 5 days. Sodium bicarbonate (4.2 g., 0.05 mol) was then added and the reaction steam distilled to remove acetophenone. The residue in the distillation flask was extracted with ethyl acetate (50 ml.), 5-cyano-4,6-dimethyl-2-pyridine separated from the mixed phases, and was removed by filtration. The organic phase was washed with hydrochloric acid (3 × 30 ml., 2 molar), and sodium carbonate solution ( 10% w/v), dried and evaporated to yield a semi-crystalline residue. The residue was crystallised from a mixture of ethyl acetate and petroleum ether (1:1 ratio; 20 ml.) to give 3,5-dicyano-1,4-dihydro-2,4,6-trimethyl-4 -phenylpyridine (1.5 g.,) as white needles, m.p. 195°–6°C. (Found: C, 76.62; H, 6.01; N, 16.46. $C_{16}H_{15}N_3$ requires C, 77.08; H, 6.06; N, 16.86%, τ (CDCl$_3$) 2.5–2.80 (5H, m phenyl protons), 2.94 (1H, s,1-H), 8.09 (6H, s,2- and 6-CH$_3$), and 8.21 (3H, s,4-CH$_3$).

I claim:

1. A dihydropyridine of formula

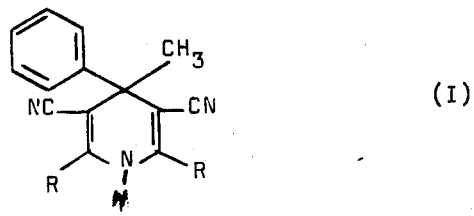

where each R is lower alkyl.

2. A dihydropyridine according to claim 1 which is 3,5-dicyano-1,4-dihydro-2,4,6-trimethyl-4-phenylpyridine.

3. A dihydropyridine according to claim 1 which is 3,5-dicyano-1,4-dihydro-2,4,6-trimethyl-4-phenylpyridine in substantially pure form.

4. A pharmaceutical preparation comprising a dihydropyridine of formula

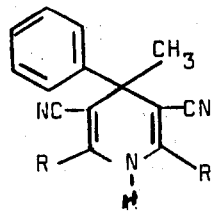

where each R is lower alkyl containing a hypotensive effective amount with an inert pharmaceutically acceptable carrier.

* * * * *